US00PP14802P3

(12) United States Plant Patent
Colfer

(10) Patent No.: US PP14,802 P3
(45) Date of Patent: May 18, 2004

(54) ARTICHOKE PLANT NAMED 'PS-IG0092'

(50) Latin Name: *Cynara scolymus*
Varietal Denomination: PS-IG0092

(75) Inventor: William J. Colfer, Aptos, CA (US)

(73) Assignee: Seed Research Services, LLC, Salinas, CA (US)

( * ) Notice: Subject to any disclaimer, the term of this patent is extended or adjusted under 35 U.S.C. 154(b) by 0 days.

(21) Appl. No.: 10/252,037

(22) Filed: Sep. 23, 2002

(65) Prior Publication Data

US 2004/0060088 P1 Mar. 25, 2004

(51) Int. Cl.[7] ..... A01H 5/00

(52) U.S. Cl. ..... Plt./258

(58) Field of Search ..... Plt./258

*Primary Examiner*—Bruce R. Campell

*Assistant Examiner*—W C Haas

(74) *Attorney, Agent, or Firm*—Foley & Lardner

(57) ABSTRACT

A new and distinct cultivar of artichoke plant named 'PS-IG0092', characterized by its moderate bud size, fleshiness of bracts, fleshiness of hearts, and uniformity of head shapes.

3 Drawing Sheets

Latin name of the genus and species of the plant claimed: *Cynara scolymus* L.
Variety denomination: PS-IG0092.

BACKGROUND OF THE INVENTION

The present invention comprises a new and distinct cultivar of artichoke plant, botanically known as *Cynara scolymus* L. and herein referred to by the cultivar name 'PS-IG0092'.

*Cynara scolymus* L., commonly known as Globe artichoke, is a thistle-like perennial herb and is a member of the family Asteraceae. Globe artichokes comprise leaves which are pinnately lobed but primarily spineless, globose capitula composed of overlapping layers of large volucral bracts, and receptacles which are enlarged and fleshy. Globe artichoke plants may be propagated by division and are essentially grown for the production of the immature flower heads, which are considered as vegetable delicacies. Fresh artichokes may be steamed or boiled, after which the fleshy receptacle, inner and outer bracts, and parts of the floral stem may be eaten.

BRIEF SUMMARY OF THE INVENTION

The new cultivar is a product of a planned breeding program carried out by the inventor, William J. Colfer at Chowchilla, Calif. in 1997. The female parent is CTC6 (seed parent) and the male parent is GG2059EC1-21-14 (pollen parent). The new cultivar was discovered from the progeny of the stated cross by William J. Colfer and was asexually propagated for the first time in 1997 in Watsonville, Calif.

Asexual propagation by division has demonstrated the stability of the combination of characteristics of the new cultivar from generation to generation.

The new cultivar has not been observed under all possible environmental conditions. The phenotype may vary with variations in environment such as temperature, light intensity and daylength, without any change in the genotype of the cultivar.

BRIEF DESCRIPTION OF THE DRAWINGS

The accompanying photographic drawings show fruit and leaves from a typical specimen plant of 'PS-IG0092', with color being depicted as accurately as possible with illustrations of this type.

The first drawing is a side view of the fruit and foliage of 'PS-IG0092'.

The second drawing is a close-up view of the fruit showing its physical dimensions.

The third drawing is a close-up view showing a vertical cross-section of the fruit.

DETAILED BOTANICAL DESCRIPTION

The following observations, measurements and values describe plants of 'PS-IG0092' grown in Chowchilla, Calif. under condition which closely approximate those generally used in horticultural practice.

The age of the plants described is approximately 240 days from transplanting. Plants were developed in transplant trays for approximately 120 days, for a total plant age of 360 days.

All color references below are measured against The Munsell Book of Color, Munsell Color Macbeth Division of Kollomogen Corporation. Colors are approximate as color depends on horticultural practices such as light level and fertilization rate, among others.

Chowchilla is located in California's central San Juaquin valley. Conditions can vary greatly during the summer months. Air temperature can range between the low 20's (degrees Fahrenheit) in the winter to well above the 100 (degrees Fahrenheit) during the summer months. Relative humidity is generally low with values ranging from the mid 40's to the high 60's. Prevailing winds are westerly and rainfall rarely exceeds 15" (inches) of rainfall.

In the following description, holding quality was measured by the physical appearance of the harvested heads. This includes the heads appearance following 3, 7 and 10 day storage periods in a cold storage room held at 34

(degrees Fahrenheit). Head exterior (oxidation) was observed at each of the three observation points. Browning and blackening of plant tissue was evaluated as light, moderate and extreme. Juiciness was measured by observing exudate and rated as absent, moderate or excessive. Overall storage response was measured by observations concentrated on visible color variability and/or presence of lesions or other cosmetic anomalies. Leaf ratio (L/W) was determined by dividing representative leaf sample length measurements by representative leaf sample width measurements. Finally, head response to (weather) was determined by observing the heads at maturity. These field observations focus on presence or absence of bronzing, necrotic and chlorotic lesions or any abiotic response to environmental conditions. These data are reported as the possible causal event(s) and then describe the detailed head and plant responses.

It should be noted that these data were collected from first year tissue culture outplants. These data are subject to change in the plant's future growth and development. The new and distinct cultivar of Artichoke plant named 'PS-IG0092' is characterized by:

1. moderate bud size;
2. fleshiness of bracts;
3. fleshiness of hearts; and
4. uniformity of head shapes.

The date of first harvest is approximately May 17 and the date of final harvest is approximately June 12, depending on environmental conditions. Plant growth from November to February is moderate, depending upon environmental and agronomic conditions. Plant growth and development from March to June is rapid, depending upon environmental and agronomic conditions, with sexual stages initiating early May.

| | |
|---|---|
| Parentage: | |
| Male parent: | GG2059EC1-21-14 (Pollen parent) |
| Female parent: | CTC6 (Seed parent) |
| Classification: | Botanical: *Cynara scolymus* L.<br>Commercial: artichoke c.v. PS-IGO092 |
| Propagation: | Asexual production standard micropropagation methodology. |
| Plant: | |
| Height: | $\bar{x}$ = 131.66 cm<br>range: 127.00–139.70 cm |
| Growth Habit: | Upright |
| Dimensions: | $\bar{x}$ = 131.66 cm (h) × 148.34 cm (w)<br>range: 127.00 cm (h) × 142.88 cm (w) |
| Side Shoots: | $\bar{x}$ = 2.00<br>range: 1.00–3.00 |
| Length of Side Shoots: | 15–26.5 cm |
| Diameter of Side Shoots: | 3.0–4.8 cm |
| Foliage Density: | Density is great in the upper and lower canopy |
| Side Shoot Development: | Moderate side shoot development |
| Number of leaves on Side Shoots: | 5–12 |
| Main Stem Length | 37–54 cm |
| Diameter of Main Stem: | 4.8–6.2 cm |
| Number of Leaves on Main Stem: | 16–26 |
| Capitulum: | |
| Size: | Primary: 33.66–35.56 cm<br>Secondary: 28.58–30.48 cm |
| Shape: | Flat, spherical. Spherical heads have broad mid-sections with a flat apex. |
| Number: | $\bar{x}$ = 5.70/plant<br>range: 3.0–8.0 heads/plant |
| Texture: | Intermediate, smooth. |
| Fragrance: | Aromatic. All bracts and upper peduncle tissues are highly aromatic, sweet odor. |
| Bract Size: | $\bar{x}$ = 6.89 cm<br>range: 6.20–7.40 cm (I) × 4.8–5.8 cm (w) |
| Bract Shape: | Bracts are predominantly oval shaped with moderate constriction on the basal portions |
| Bract Texture; | Smooth, very-slight texture |
| Bract Number: | $\bar{x}$ = 50.80 bracts<br>range: 48–54 bracts |
| Bract Color: | Inner: 2.5 GY 9/2–2.5 GY 9/4<br>Outer: 5 GY 9/2–5 GY 8/4 |
| Bract Basal Thickness: | $\bar{x}$ = 7.58 mm<br>range: 5.0–9.0 mm |
| Heart Description: | Concave, full. Heart dimensions are broad and thick in the outer portions of the heart. |
| Heart Color: | 7.5 Y 9/2 |
| Papus Length: | $\bar{x}$ = 11.83 mm<br>range: 10.0–13.0 mm |
| Papus Color: | Variable white coloration. Papus turns slightly golden as it oxidizes. |
| Overall Cold Storage Response: | Good. Those areas damaged during harvest did blacken, seems to oxidize rapidly. |
| Head Firmness: | Firm. Heads maintain good firmness during maturation. |
| Bract Firmness: | Malleable. Bracts are malleable and flexible. |
| Gloss: | Dull. Heads have a distinct opaque, chlorotic spine - line pattern that is slightly spherical. |
| Cold Storage (hold quality): | Good cold storage response. Slight oxidation observed (browning). |
| Head Exterior (oxidation): | Moderate. Bruised and harvest damaged region blacken and oxidize quickly. |
| Juiciness: | Moderate presence. Beduncle and bract tissues have moderate juice presence following cutting and tissue removal. |
| Head Response (weather): | No adverse head response were observed. |
| Bud Burst: | Between May 15 and June 28 |
| Bud Weight: | 457.65–471.90 grams: average 461.23 grams per head |
| Bloom Time: | June 4 and July 1 |
| Bloom Duration: | From June 4 to July 7 |
| Bloom Diameter | 10.5–11.2 cm<br>11–11.7 cm |
| Bloom Shape | Head (slightly rounded oval) |
| Floret Number per Bloom | Approximately 1474–1556 |
| Floret Size: | 7.0–7.3 cm in length<br>3.0–3.1 mm in width |
| Floret Color | Range between 2.5P 7/8–2.5P 6/8–2.5P 5/10–2.5P 5/8 |
| Seeds: | |
| Shape: | Ovate |
| Size: | 0.7–0.8 mm in length:<br>0.35–0.4 mm in width |
| Number: | Highly variable between 85–447: average 226 seeds per head |
| Coloration: | Variable light browm and gray hues with moderate speckling: some darker black coloration without speckled pattern |
| Foliage: | |
| Shape | Irregularly dentate, pinnatisect, reduced tomentose and slightly reduced mucronulate |
| Length: | $\bar{x}$ = 11.38 cm<br>range: 97.6–119.4 cm |

-continued

| | |
|---|---|
| Width | $\bar{x}$ = 63.65 cm<br>range: 59.1–68.7 cm |
| Leaf Serrations: | $\bar{x}$ = 47.19 cm<br>range: 25.0–77.0 cm |
| Leaf Basal Angle: | $\bar{x}$ = 40.83 degrees<br>range: 30–55 degrees |
| Leaf Ratio (L/W): | $\bar{x}$ = 1.77<br>range: 1.50–2.01 |
| Leaf Area: | $\bar{x}$ = 7,154 $cm^2$<br>range: 6173.2–8155.0 $cm^2$ |
| Color: | 5 GY 4/2–5 GY 4/4–5 GY 3/6 |
| Texture: | Smooth–slightly textured range. Leaf color gives the leaf a soft, smooth appearance. |
| Veination: | Intermediate, greenish. Veination is distinct, but light green in color. |
| Pubescence: | Leaf pubescence is dense giving leaf a soft, supple appearance. |
| Leaf Basal Thickness | $\bar{x}$ = 17.47 cm<br>range: 15.0–23.0 mm |
| Leaf Distance Between Serrations:<br>range: 30.0–65.0 mm | $\bar{x}$ = 42.97 mm |
| Petiole Length:<br>range: 20.1–28.2 cm | $\bar{x}$ = 23.43 cm |
| Petiole Width:<br>range: 3.0–4.0 cm | $\bar{x}$ = 3.50 cm |
| DISEASE RESISTANCE: | No observations made |

General observations:

This new artichoke cultivar is a unique type that exhibits the following characteristics. The plants moderate height, ranging from 127–139 cm. Its comparative head qualities to California's artichoke variety Green Globe include: green (non-glossy) exterior coloration, comparable head numbers. Head numbers ranging from 3–8 heads per plant. Head shape does vary displaying a pronounced flat, spherical shape. These non-glossy heads are produced in the sizes ranging from (18) primary, size (30) secondaries and size (48) tertiaries. Floral stalk development and head numbers can vary. Anthocyanin coloration is present in innermost interior bracts and found on only some outer, exterior bract edges. Its presence is characterized as light. The head spinosity is slightly more prominent on these notched bracts. The average spine length ranges between 1.5–2.0 mm. The plants upright growth habit is intermediate, but is very vigorous. The canopies coloration is a deeper green/green/yellow color with some colors ranging towards darker green/green/grey hues. These colors on Munsell Leaf Color Chart range from 5 GY 4/2–5 GY 4/4–5 GY 3/6. Leaf spinosity is light to moderate, categorized as few. Floral stalk development during anthesis produces a purple flower. Flower color varies with flower maturity. The phenotypic characteristics of this cultivar may vary slightly, depending upon variation in the environmental factors. Including weather (temperature, humidity and light intensity), day length, soil type, farming practices, location and time of year.

I claim:

1. A new and distinct cultivar of artichoke plant named "PS-IG0092", as described and illustrated.

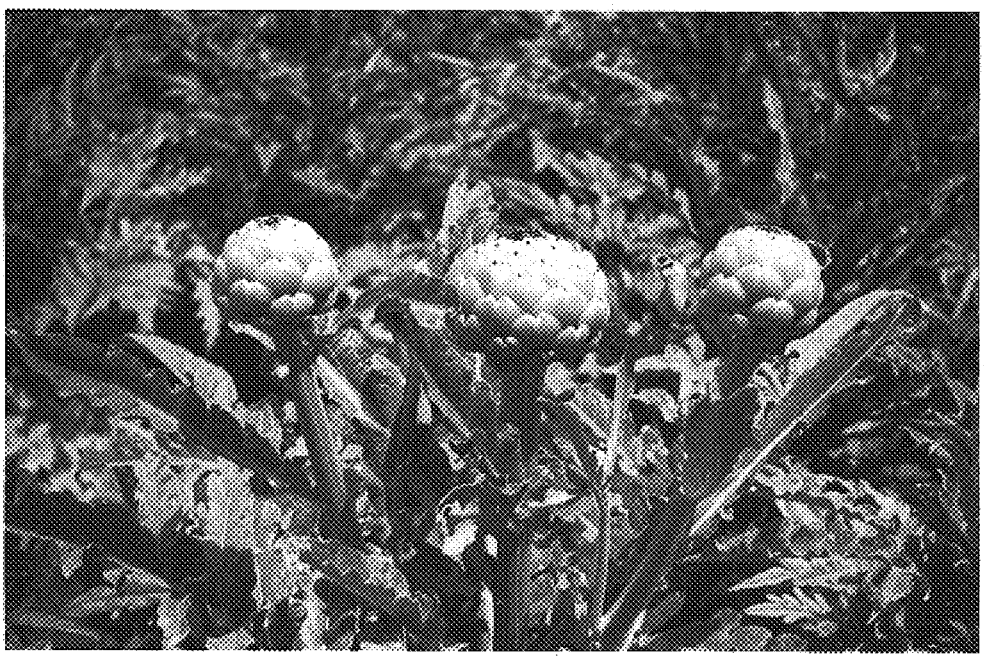

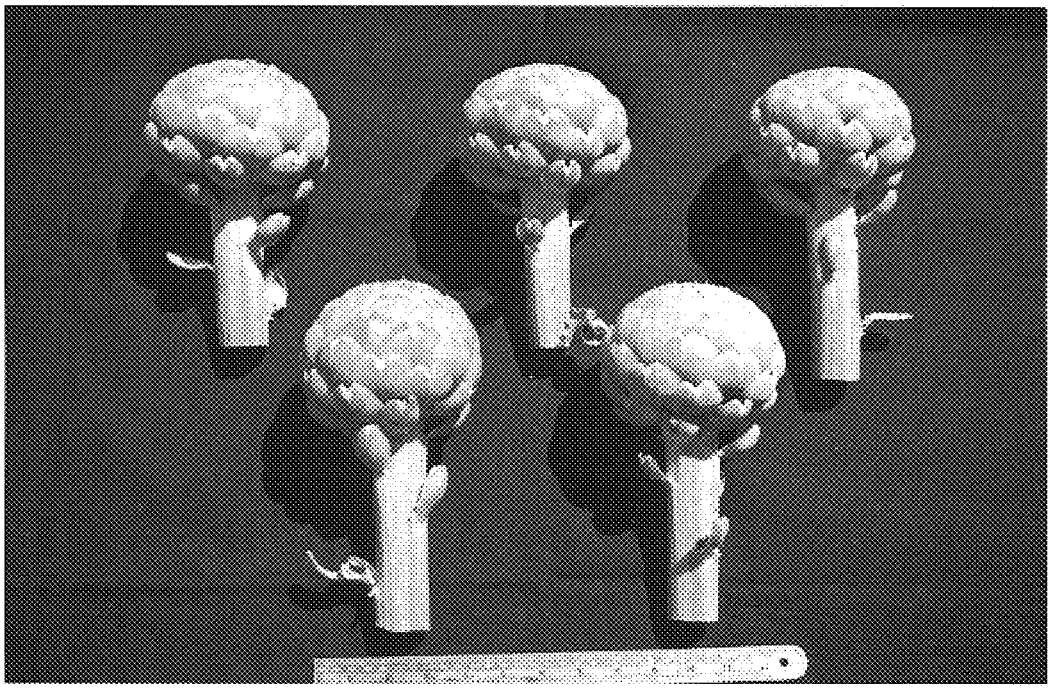

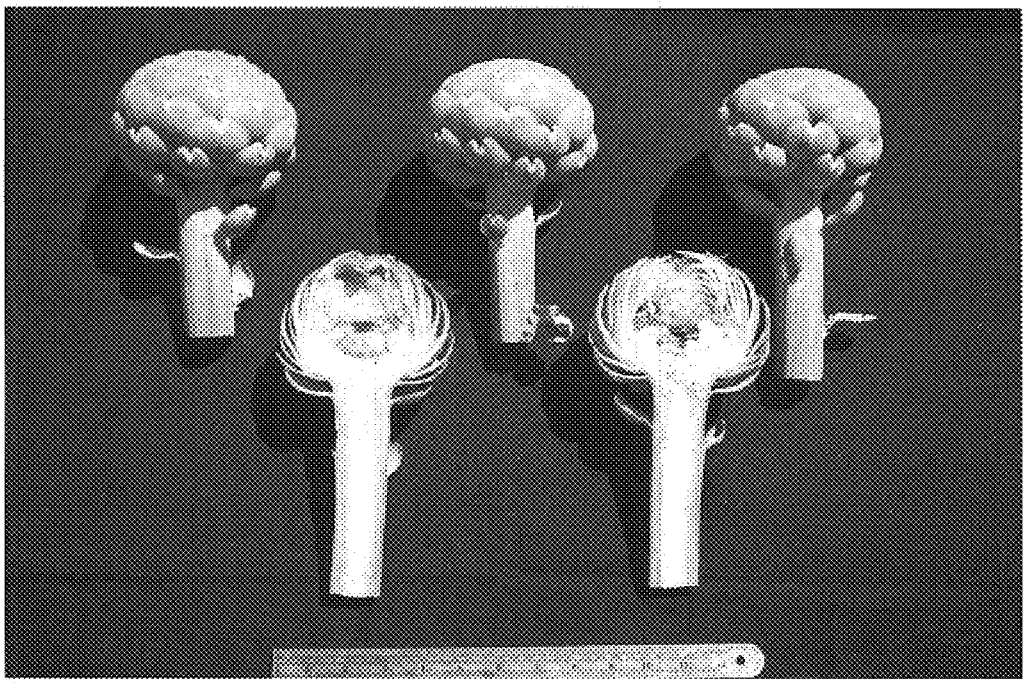

* * * * *